US006806375B2

(12) United States Patent
Freer et al.

(10) Patent No.: US 6,806,375 B2
(45) Date of Patent: Oct. 19, 2004

(54) PROCESS FOR THE PRODUCTION OF PURINE DERIVATIVES AND INTERMEDIATES THEREFOR

(75) Inventors: Richard Freer, Bishop's Stortford (GB); Graham Richard Geen, Dunmow (GB); Thomas Weir Ramsay, Haverhill (GB); Andrew Colin Share, Saffron Walden (GB); Neil Michael Smith, Saffron Walden (GB)

(73) Assignee: Novartis International Pharmaceutical Ltd., Hamilton (BM)

(*) Notice: Subject to any disclaimer, the term of this patent is extended or adjusted under 35 U.S.C. 154(b) by 0 days.

(21) Appl. No.: 10/369,841

(22) Filed: Feb. 19, 2003

(65) Prior Publication Data

US 2003/0130512 A1 Jul. 10, 2003

Related U.S. Application Data

(62) Division of application No. 09/623,662, filed as application No. PCT/EP99/02308 on Mar. 30, 1999, now Pat. No. 6,555,685.

(30) Foreign Application Priority Data

Apr. 2, 1998 (GB) ............................................... 9807114

(51) Int. Cl.[7] .................... C07D 473/18; C07D 473/32; C07D 473/40; C07D 319/06; C07F 7/18
(52) U.S. Cl. ........................................ 549/372; 549/221
(58) Field of Search ................................ 549/369, 371, 549/372

(56) References Cited

U.S. PATENT DOCUMENTS

| 4,798,833 A | 1/1989 | Johansson .................... 514/262 |
| 5,036,071 A | 7/1991 | Johansson et al. .......... 514/261 |

FOREIGN PATENT DOCUMENTS

| EP | 0 146 516 | 6/1985 |
| EP | 0 186 640 | 7/1986 |
| EP | 0 352 953 | 1/1990 |
| WO | 95/28402 | 10/1995 |

OTHER PUBLICATIONS

Somei, Heterocycles 26(11) 2823–8 1987.*
Baskov, Bull. de l'Academie Polonaise des Sci, Serie description Science Chim. 19(11–12) 681–3 1971.*
Haines et al., "Synthesis and Biological Activity of Unsaturated Carboacyclic Purine Nucleoside Analogues", J. Med. Chem., vol. 30, No. 5, pp. 943–947 (1987).
Rondestvedt, Jr. et al., "A New Rearrangement. Catalytic Isomerization of m–Dioxanes to β–Alkoxy Aldehydes. II. Scope and Limitations", J. Am. Chem. Soc., vol. 84, pp. 3307–3319 (1962).

* cited by examiner

*Primary Examiner*—Mark L. Berch
(74) *Attorney, Agent, or Firm*—Thomas R. Savitsky

(57) ABSTRACT

Intermediates such as methyl 2,2-dimethyl-5-ethenyl-1,3-dioxane-5-carbonate useful to prepare antiviral compounds such as penciclovir and famciclovir are disclosed.

5 Claims, No Drawings

PROCESS FOR THE PRODUCTION OF PURINE DERIVATIVES AND INTERMEDIATES THEREFOR

This application is a Divisional of U.S. patent application Ser. No. 09/623,662, filed Nov. 1, 2000, now U.S. Pat. No. 6,555,685, which is a 371 of PCT Application No. PCT/EP99/02308, filed Mar. 30, 1999, which is herein incorporated by reference.

Nucleosides and Nucleotides, 15(5), 981–994 (1996) and WO 95/28402 disclose a process for the manufacture of the anti-viral agents 9-(4-acetoxy-3-acetoxymethylbut-1-yl)-2-aminopurine (famciclovir) and 9-(4-hydroxy-3-hydroxymethylbut-1-yl)guanine (penciclovir). According to this process, the 'bromoester' route, 2-amino-6-chloropurine is reacted with triethyl 3-bromopropane-1,1,1-tricarboxylate in the presence of base to form diethyl 2-[2-(2-amino-6-chloropurin-9-yl)ethyl]-2-carboxymalonate. The crude isolate from this alkylation reaction is then treated with sodium methoxide in methanol to form dimethyl 2-[2-(2-amino-6-chloropurin-9-yl)ethyl]malonate. This product is purified by crystallisation and then successively reduced using sodium borohydride and O-acetylated to give 9-(4-acetoxy-3-acetoxymethylbutyl)-2-amino-6-chloropurine. Famciclovir is produced directly from the latter compound by hydrogenation over a supported palladium catalyst; and penciclovir is produced from this compound by acid hydrolysis of the acetoxy groups.

A disadvantage of this route to famciclovir and penciclovir is that the initial alkylation reaction with the bromotriester reagent gives a mixture of the N-9 and N-7 isomers. 2-Amino-6-chloropurine is a fairly expensive starting material, and accordingly the wastage arising from the production of the unwanted N-7 isomer is undesirable.

EP-A-0352953 discloses a process for the production of purine derivatives according to the bromotriester route in which the ratio of N-9 to N-7 products is improved by converting the 2-amino-6-chloropurine to the analogous 6-iodo, 6-benzylthio or 6-(phenacylmethyl)thio compound.

Whilst the process of EP-A-0352953 represents an improvement in the bromotriester process for producing famciclovir, it suffers from the disadvantages that a material quantity of the N-7 isomer still results, and moreover an additional step of converting the 6-chloro substituent to 6-iodo, 6-benzylthio or 6-(phenacylmethyl)thio is required.

Accordingly, there remains a need for an improved process for making purine derivatives such as famciclovir and penciclovir.

According to one aspect of the invention there is provided a process for the production of a compound of formula (I):

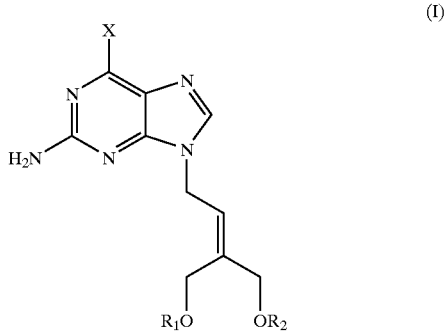

(I)

wherein X is H, OH or halo; and $R_1$ and $R_2$ are selected independently from $C_{1-12}$ alkyl, aryl, $C_{1-12}$ alkylaryl, $C_{1-12}$ alkylsilyl, arylsilyl and $C_{1-12}$ alkylarylsilyl, or $R_1$ and $R_2$ are joined together to form a cyclic acetal or ketal; which process comprises reacting a compound of formula (II):

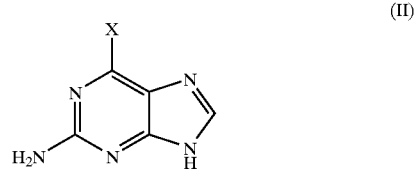

(II)

wherein X is as defined for formula (I), with a compound of formula (III):

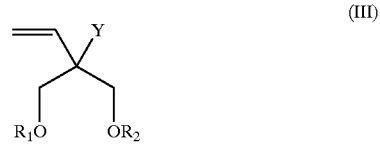

(III)

wherein Y is a leaving group and $R_1$ and $R_2$ are as defined for formula (I), in the presence of a palladium(0) catalyst and a ligand.

Preferably X is halo, more preferably X is chloro.

$R_1$ and $R_2$ may be selected independently from benzyl and $C_{1-12}$ alkyldiarylsilyl, such as $C_{1-6}$ alkyldiphenylsilyl, e.g. t-butyldiphenylsilyl. Preferably however, $R_1$ and $R_2$ are linked to form a cyclic acetal or ketal, preferably a 6-membered cyclic acetal or ketal of formula (IV):

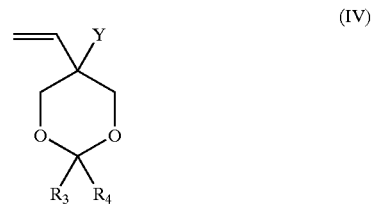

(IV)

wherein $R_3$ and $R_4$ are selected independently from H, $C_{1-12}$ alkyl and aryl.

Preferably $R_3$ and $R_4$ are both $C_{1-12}$ alkyl, more preferably $R_3$ and $R_4$ are both methyl.

The palladium (0) catalyst may be selected from tetrakis (triphenylphosphine) palladium(0), tris (dibenzylideneacetone)dipalladium(0) chloroform or any palladium(0) dibenzylidene catalyst. More generally it is envisaged that any palladium(0) source may be suitable.

Alternatively the palladium(0) catalyst may be formed in situ from a palladium(II) salt. The salt may be selected from palladium acetate, palladium chloride, allyl palladium chloride dimer, bis(triphenylphosphine) palladium chloride and [1,2-bis(diphenylphosphino)ethane]dichloropalladium (II).

The ligand may be selected from the group consisting of triphenylphosphine; tributylphosphine; tricyclohexylphosphine; bis(diphenylphosphino)methane; 1,2-bis(diphenylphosphino)ethane; 1,3-bis(diphenylphosphino) propane; 1,4-bis(diphenylphosphino)butane; 1,2-bis(diphenylphosphino)ferrocene; (R)-(+)-2,2'bis(diphenylphosphino)-1,1'-binaphthyl; 3,3'3"-phosphinidynetris(benzenesulphonic acid) trisodium salt; trimethyl phosphite; triisopropyl phosphite; triphenyl phosphite, trimethylolpropane phosphite, tri-2-furylphosphine and tris(4-methoxyphenyl)phosphine.

Preferably, the ligand is selected from 1,2-bis (diphenylphosphino)ethane [DIPHOS], trimethylolpropane phosphite [TMPP] and 1,3-bis(diphenylphosphino)propane [DPPP].

The reaction between the compound of formula (II) and the compound of formula (III) may additionally be conducted in the presence of a base. The base may selected from caesium carbonate, potassium carbonate, sodium carbonate, lithium carbonate, cesium fluoride, lithium hydride, sodium hydride, sodium hydroxide, triethylamine, diazabicyclo [5.4.0]undec-7-ene and 1,1,3,3-tetramethylguanidine. The base is preferably caesium or potassium carbonate.

Where the catalyst is provided in the form of a palladium (II) salt, which is reduced to palladium(0) in situ, the reaction may be effected by the phosphine or phosphite ligand, or by the use of an additional reducing agent. It has been found, for example, that the TMPP ligand is capable of reducing the palladium(II) salt to palladium(0) to give a good N-9 to N-7 ratio. The additional reducing agent may be selected from hydrazine and sodium hypophosphite.

The reaction will usually be conducted in an inert solvent. The inert solvent may be selected from the group consisting of dimethylformamide (DMF), diethylformamide, N-methylpyrrolidinone, dimethylacetamide, dimethylsulphoxide, acetonitrile, tetrahydrofuran, aqueous methanol, aqueous acetonitrile and aqueous dimethylformamide. Preferably the inert solvent comprises DMF.

The reaction may be carried out at a temperature in the range of about 20–120° C., preferably about 60–80° C., for 1–50 hours depending on the reagents used, preferably 1–24 hours.

The reaction may be conducted under an inert atmosphere. Any suitable inert gas may be used, but argon is preferred. Preferably the reaction is carried out under a flow of the inert gas.

Further additives may be included in the reaction mixture, which additives are selected from hydrazine hydrate, benzyltrimethylammonium chloride, tetrabutylammonium chloride, magnesium iodide, Aliquat 336, barium acetate, lithium chloride, 15-Crown-5, ammonium formate, sodium acetate, sodium hypophosphite hydrate and n-butyllithium.

The reaction may be performed by adding the palladium catalyst to a reaction mixture containing the compounds of formulae (II) and (III), the ligand and any additional reagents, such that the ligated catalytic species is formed in situ. However, pre-formation of the ligated catalytic species is preferred. Pre-formation may be achieved by stirring the palladium catalyst and the ligand in the reaction solvent, e.g. for a period of up to 30 min, prior to the addition of the compounds of formulae (II) and (III) and any additional reagents.

It has been found surprisingly that the reaction between compounds of formulae (II) and (III) in accordance with the present invention gives rise to a very high yield of the N-9 isomer over the unwanted N-7 isomer.

In a further aspect of the invention there is provided a compound of formula (I) which is a novel intermediate wherein X, $R_1$ and $R_2$ are as defined above.

In another aspect of the invention there is provided a process for the production of a compound of formula (V):

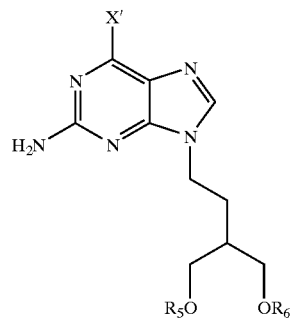

wherein X' is H or OH; and $R_5$ and $R_6$ are independently selected from H and R'CO wherein R' is phenyl, $C_{1-12}$ alkyl or phosphoryl, which process comprises producing a compound of formula (I) according to the process of the invention defined above, hydrogenating the compound of formula (I), converting —$OR_1$ and —$OR_2$ to form two hydroxy groups and thereafter if and as necessary:

(i) converting one or both of the hydroxy groups on the resulting 4-hydroxy-3-hydroxymethylbut-1-yl moiety to form compounds in which $R_5$ and $R_6$ represent R'CO; and/or (ii) converting X to X'.

Preferably $R_5$ and $R_6$ are both hydrogen or acetyl. Where X' is H and $R_5$ and $R_6$ are both acetyl the compound of formula (V) is famciclovir. Where X' is OH and $R_5$ and $R_6$ are both H the compound of formula (V) is penciclovir.

Hydrogenation of the ethylidene moiety may be effected by hydrogenation of the compound of formula (I) in the presence of a catalyst, preferably a palladium catalyst, such as palladium on charcoal. Other suitable catalysts are $Pd/CaCO_3$ and $Pd(OH)_2/C$. The hydrogenation may be carried out in a solvent selected from the group consisting of alkyl esters e.g. ethyl acetate, tetrahydrofuran, and $C_{1-6}$ alkyl alcohols e.g. methanol or ethanol.

Optionally a base is included in the reaction mixture. The base may be selected from triethylamine, sodium acetate, potassium hydroxide, aqueous sodium hydroxide and basic alumina. Alternatively a basic ion exchange resin may be employed. Hydrogenation may be carried out at elevated temperature and pressure or, alternatively, at room temperature and atmospheric pressure. As mentioned above, X is preferably halo such as chloro. In accordance with an important aspect of the invention, hydrogenation of the compound of formula (I) in the presence of a base reduces both the chloro moiety (to H) at the 6-position on the purine ring and also the double bond. This one step reduction of the 6-chloro and ethylidene groups represents a particularly advantageous synthetic route to famciclovir. The reduced product may be isolated if required. In the absence of base, only the double bond is reduced. Subsequent hydrolysis of the 6-chloro group and —$OR_1$ and —$OR_2$ then affords penciclovir. Therefore, the choice of whether or not to use a base allows the synthesis of either famciclovir or penciclovir.

—$OR_1$ and —$OR_2$ may be converted to —OH by any suitable method known to those skilled in the art. Cyclic acetals or ketals are preferably hydrolysed using tetrahydrofuran/methanol and hydrochloric acid. Where $R_1$ and $R_2$ are benzyl, then hydrogenation may be used.

In a particularly preferred embodiment of this aspect of the invention, the two hydroxy groups of the 4-hydroxy-3-hydroxymethylbut-1-yl group are acylated. Any convenient acylation method known to those skilled in the art may be used, but preferably acetic anhydride is employed.

The 2-amino group on the purine ring may be protected throughout using conventional protecting groups such as benzyl, acetyl or a Schiff's base.

Various of the compounds of formula (III) are novel, thus according to a further aspect of the invention there is provided a compound of formula (III):

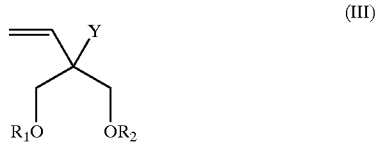

(III)

wherein Y is a leaving group and $R_1$ and $R_2$ are are joined together to form a cyclic acetal or ketal.

A preferred group of compounds of formula (III) are those of formula (IV):

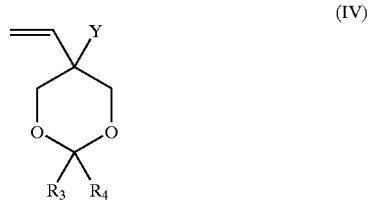

(IV)

wherein Y is a leaving group and $R_3$ and $R_4$ are selected independently from H, $C_{1-12}$ alkyl and aryl. Preferably $R_3$ and $R_4$ are both $C_{1-12}$ alkyl, more preferably $R_3$ and $R_4$ are both methyl.

A particular compound of formula (III) that may be mentioned is methyl 2,2-dimethyl-5-ethenyl-1,3-dioxane-5-carbonate.

The compounds of formula (III) may be prepared by reacting a compound of formula (VI):

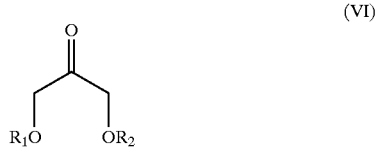

(VI)

wherein $R_1$ and $R_2$ are as defined for formula (I), with a vinyl carbanion and thereafter converting the resulting alkoxide to the leaving group Y.

The vinyl carbanion may be a Grignard reagent such as vinylmagnesium bromide.

The nucleophilic addition of the vinyl carbanion to the compound of formula (VI) may be carried out in an inert solvent such as tetrahydrofuran, at a temperature of less than about −60° C., preferably about −78° C.

The leaving group Y may be selected from the group consisting of $C_{1-6}$ alkyl- or aryl carbonates e.g. methyl carbonate or phenyl carbonate, $C_{1-6}$ acyloxy e.g. acetate or trifluoroacetate, and $C_{1-6}$ alkylphosphates e.g. diethylphosphate. A $C_{1-6}$ alkyl carbonate is preferred however because it gives rise to volatile side products when reacted with the compound of formula (II). The leaving group may be introduced by, for example, quenching the reaction between the compound of formula (VI) and the vinyl carbanion with a $C_{1-6}$ alkyl chloroformate, e.g. methyl chloroformate, if desired. The 5-vinyl-5-hydroxy intermediate formed by reaction of the vinyl carbanion with the compound of formula (VI) may be isolated before the leaving group Y is introduced. The compound of formula (III) may be isolated and purified by known methods. Alternatively, the compound of formula (III) may be used as a crude oil without purification.

Unless otherwise stated, any of the alkyl groups mentioned above may comprise 1–12 carbon atoms, preferably 1–6 carbon atoms. Alkyl groups may be straight or branched chain, or cyclic. Cyclic alkyl groups preferably comprise 3–8 carbon atoms. Any alkyl groups may be substituted by one or more fluoro atoms.

Any of the aryl groups mentioned above preferably comprise 5–10 carbon atoms and may be mono- or bicyclic. Suitable aryl groups included phenyl and naphthyl, preferably phenyl.

All publications, including but not limited to patents and patent applications, cited in this specification are herein incorporated by reference as if each individual publication were specifically and individually indicated to be incorporated by reference herein as though fully set forth.

There follows a description by way of example only of embodiments of the present invention.

EXAMPLE 1

Preparation of Methyl 2,2-dimethyl-5-ethenyl-1,3-dioxane-5-carbonate 2,2-Dimethyl-1,3-dioxan-5-one (38.0 g) in tetrahydrofuran (250 ml) was added dropwise to a 1 M solution of vinylmagnesium bromide in tetrahydrofuran (700 ml) under argon maintaining a temperature of less than −60° C. The reaction mixture was cooled to −78° C. and stirred at this temperature for 0.5h. Methyl chloroformate (75 ml) was added dropwise and the resulting mixture stirred at −78° C. for 0.25 h before being allowed to warm to room temperature. The solvent was removed by evaporation under reduced pressure. Ethyl acetate (2×500 ml) was added to the residue and the solvent removed by distillation after each addition. The residue was stirred in ethyl acetate/hexane 40:60 and the resulting mixture passed through a short silica column. The column was washed with further ethyl acetate/hexane 40:60 (2×1.0 L) and the combined fractions concentrated to give an oil. The crude oil was purified by silica column chromatography (eluent hexane/ethyl acetate 90:10 increasing to hexane/ethyl acetate 85:15) to give the title compound as a pale yellow oil (46 g, 73% yield).

$^1$Hnmr (CDCl$_3$): δ 6.0 (dd, 1H, CH); 5.3 (m, 2H, CH$_2$); 4.05 (abq, 4H, 2×CH$_2$); 3.75 (s, 3H, OCH$_3$); 1.45 (s, 3H, CH$_3$); 1.4 (s, 3H, CH$_3$)

EXAMPLE 2

Example 1 was repeated except that, as an alternative to purification by column chromatography, the methyl 2,2-dimethyl-5-ethenyl-1,3-dioxane-5-carbonate was purified by distillation at 78° C. and 0.6 mmHg.

EXAMPLE 3

Example 1 was repeated, except that the reaction mixture was poured into 1M potassium dihydro-orthophosphate then extracted into diethyl ether and purified by column chromatography.

EXAMPLE 4

Example 1 was repeated, except that the reaction mixture was concentrated and the residue slurried in diethyl ether and saturated brine. The ether layer was concentrated, and the residue purified by column chromatography.

EXAMPLE 5

Preparation of 5-[2-(2-amino-6-chloropurin-9-yl)]ethylidene-2,2-dimethyl-1,3-dioxane Methyl 2,2-dimethyl-5-ethenyl-1,3-dioxane-5-carbonate (6.48 g), 2-amino-6-chloropurine (5.1 g), cesium carbonate (9.9 g) and trimethylolpropane phosphite (0.48 g) were stirred in dimethylformamide (300 ml) at 20–25° C. under argon. Tris(dibenzylideneacetone)dipalladium(0) chloroform (0.78 g) was added and the resulting mixture heated to 60° C. and stirred at this temperature for 3 hours. The inorganic solids were removed by filtration through celite, the filter washed with dimethylformamide (50 ml) and the combined filtrate and wash concentrated under reduced pressure to give a brown oil. The oil was dissolved in dichloromethane and the precipitated polymeric products removed by filtration. The product was purified by silica gel column chromatography (eluent dichloromethane/methanol 97:3) to give the title compound as an off-white solid (6.1 g, 66% yield).

$^1$Hnmr (DMSO-$d_6$): δ 8.1 (s, 1H, CH); 6.9 (s, 2H, $NH_2$); 5.5 (t, 1H, CH); 4.6 (d, 2H, $CH_2$); 4.5 (s, 2H, $CH_2$); 4.2 (s, 2H, $CH_2$); 1.3 (s, 6H, 2×$CH_3$) mp 157–159° C.

EXAMPLE 6

Example 5 was repeated, except that after removal of the inorganic solids, the dimethylformamide solution of products was concentrated under reduced pressure. The residue was dissolved in hot methanol (5 volumes) and the solution cooled to 5° C. The product was collected by filtration, washed with methanol and dried in vacuo (1.62 g, 48% yield).

EXAMPLE 7
Pre-formation of Ligated Catalytic Species 1,2-Bis(diphenylphosphino)ethane (0.378 g) was dissolved in dimethylformamide (22 ml) under argon. Tris(dibenzylideneacetone)dipalladium (0) (0.435 g) was added, the resulting solution degassed under vacuum and stirred under argon for 10 min. The pre-formed catalytic species was added to a stirred suspension of methyl-2,2-dimethyl-5-ethenyl-1,3-dioxane-5-carbonate (4.32 g), 2-amino-6-chloropurine (3.21 g) and caesium carbonate (0.063 g) in degassed dimethylformamide (45 ml) all under argon at room temperature. The mixture was heated to 80° C. and stirred at this temperature for 7.5 hours. After standing overnight at room temperature the reaction mixture was filtered and concentrated to give a gummy solid which was slurried and recrystallised from methanol to give the desired product (4.2 g, 72% yield).

EXAMPLE 8

Methyl-2,2-dimethyl-5-ethenyl-1,3-dioxane-5-carbonate (1.5 g), 2-amino-6-chloropurine (1.07 g), caesium carbonate (0.208 g) and 1,2-bis(diphenylphosphino)ethane (0.126 g) were stirred in dimethylformamide (22.3 ml) at 20–25° C. under argon. Tris(dibenzylideneacetone)dipalladium (0) (0.145 g) was added and the resulting mixture heated to 80° C. and stirred for 4 hours. The reaction mixture was filtered and the filtrate concentrated under reduced pressure. The residue was dissolved in dichloromethane and the product purified by silica gel column chromatography (eluent dichloromethane/methanol 97:3) to give the desired product as an off-white solid (1.6 g, 81% yield).

EXAMPLE 9
Preparation of 5-[2-(2-aminopurin-9-yl)ethyl]-2,2-dimethyl-1,3-dioxane A mixture of 2,2-dimethyl-5-[2-(2-amino-6-chloropurin-9-yl)]ethylidene-1,3-dioxane (0.45 g), 5% palladium on carbon (0.225 g) and triethylamine (0.22 ml) in ethyl acetate (22.5 ml) was hydrogenated at 50° C. for 18 hours at 50 p.s.i. The catalyst was removed by filtration and the filter washed with ethyl acetate. The combined filtrate and wash were concentrated under reduced pressure to give a gum which was purified by silica gel chromatography (eluted with dichloromethane/methanol 99:1 increasing to 97:3) to give the title compound (300 mg, 74% yield).

$^1$Hnmr (DMSO-$d_6$): δ 8.6 (s, 1H, CH); 8.1 (s, 1H, CH); 6.5 (s, 2H, $NH_2$); 4.1 (t, 2H, $CH_2$); 3.8–3.5 (m, 4H, 2×$CH_2$); 1.73 (q, 2H, $CH_2$); 1.6 (m, 1H, CH); 1.3 (s, 3H, $CH_3$); 1.25 (s, 3H, $CH_3$)

EXAMPLE 10
Preparation of 5-[2-(2-amino-6-chloropurin-9-yl)ethyl]-2,2-dimethyl-1,3-dioxane 5% Palladium on carbon (1.5 g) in tetrahydrofuran (40 ml) was prehydrogenated for 30 min at 50 p.s.i. 2,2-Dimethyl-5-[2-(2-amino-6-chloropurin-9-yl)]ethylidene-1,3-dioxane (3.0 g) in tetrahydrofuran (80 ml) was added and washed in with tetrahydrofuran (30 ml). The mixture was hydrogentated overnight at 50 p.s.i. with stirring. The catalyst was removed by filtration to give a colourless solution. The solvent was removed under reduced pressure and the residue recrystallised from IPA to give the title compound (1.92 g, 62.2% yield).

Analysis: Found C: 49.98; H: 5.82; N: 22.42%; Required: C: 50.08; H: 5.82; N: 22.46%. 5-[2-(2-Amino-6-chloropurin-9-yl)ethyl]-2,2-dimethyl-1,3-dioxane can be converted to penciclovir using techniques known in the art such as those described in EP 141927.

EXAMPLE 11
Preparation of 2-amino-9-(4-hydroxy-3-hydroxymethylbut-1-yl)purine hydrochloride To a stirred solution of 2,2-dimethyl-5-[2-(2-aminopurin-9-yl)ethyl]-1,3-dioxane (1 g) in a mixture of tetrahydrofuran (20 ml) and methanol (6 ml) at room temperature was added concentrated hydrochloric acid (0.32 ml). The resulting mixture was stirred for 2 hours during which time a solid crystallised. The solid was collected by filtration, washed with tetrahydrofuran (2 ml) and dried under a flow of air to give the desired product as the hydrochloride salt (800 mg, 81% yield).

$^1$Hnmr (DMSO-$d_6$/$D_2O$): δ 8.9 (s, 1H, CH); 8.6 (s, 1H, CH); 4.2 (t, 2H, $CH_2$); 3.5–3.3 (m, 4H, 2×$CH_2$); 1.8 (q, 2H, $CH_2$); 1.5 (m, 1H, CH) mp 174–176° C.

EXAMPLE 12
Preparation of 9-(4-acetoxy-3-acetoxymethylbut-1-yl)-2-aminopurine (Famciclovir)

To a stirred suspension of 2-amino-9-(4-hydroxy-3-hydroxymethylbut-1-yl)purine hydrochloride (0.79 g), 4-dimethylaminopyridine (16 mg) and triethylamine (1.4 ml) in dichloromethane (16 ml) at room temperature was added acetic anhydride (0.57 ml). The resulting mixture was stirred at ambient temperature for 2.25 hours. Methanol (4 ml) was added and the solution stirred for 0.5 hours before being evaporated to dryness. Water (20 ml) was added and the aqueous solution extracted with dichloromethane (3×20 ml). The combined extracts were concentrated to give an oil. This oil was dissolved in 2-propanol (5 ml), the solvent evaporated and the residue recrystallised from 2-propanol (5 ml). The product was collected by filtration, washed with 2-propanol (3 ml) and dried to give the title compound (654 mg, 70%).

$^1$Hnmr (DMSO-$d_6$): δ 8.6 (s, 1H, CH); 8.1 (s, 1H, CH); 6.5 (s, 2H, $NH_2$); 4.1 (t, 2H, $CH_2$); 4.0 (d, 4H, 2×$CH_2$); 2.0 (s, 6H, 2×$CH_3$); 1.9 (m, 3H, CH and $CH_2$)

What is claimed is:

1. A compound of formula (III):

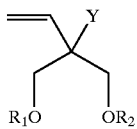
(III)

wherein Y is selected from the group consisting of $C_{1-6}$alkyl- or aryl carbonates. $C_{1-6}$acyloxy and $C_{1-6}$alkylphosphates; and $R_1$ and $R_2$ are joined together to form a moiety of the formula

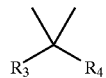

wherein $R_3$ or $R_4$ are selected independently from H, $C_{1-12}$ alkyl and aryl.

2. A compound according to claim 1 wherein Y is selected from the group consisting from methyl carbonate, phenyl carbonate, acetate, trifluoroacetate and diethylphosphate.

3. A compound according to claim 2 wherein $R_3$ and $R_4$ are $C_{1-12}$alkyl groups.

4. A compound according to claim 2 wherein $R_3$ and $R_4$ are methyl groups.

5. A compound which is methyl 2,2-dimethyl-5-ethenyl-1,3-dioxane-5-carbonate.

* * * * *